US009012674B1

(12) United States Patent
Neary et al.

(10) Patent No.: US 9,012,674 B1
(45) Date of Patent: *Apr. 21, 2015

(54) ETHYL (2R)-2-ACETAMIDO-3-(4-METHYLBENZOYL SULFANYL)PROPANOATE AND USES THEREOF (71) Applicant: Promentis Pharmaceuticals, Inc., Milwaukee, WI (US)

(72) Inventors: Michael Neary, West Allis, IL (US); James Nieman, Sherwood Park (CA); Steven Tanis, Carlsbad, CA (US); Daniel Lawton, Bayside, WI (US)

(73) Assignee: Promentis Pharmaceuticals, Inc., Milwaukee, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,953

(22) Filed: Nov. 7, 2014

Related U.S. Application Data (60) Provisional application No. 61/902,052, filed on Nov. 8, 2013, provisional application No. 61/902,669, filed on Nov. 11, 2013.

(51) Int. Cl.
*C07C 327/34* (2006.01)
*A61K 31/265* (2006.01)
*C07C 327/00* (2006.01)

(52) U.S. Cl.
CPC .............. *C07C 327/34* (2013.01); *A61K 31/265* (2013.01)

(58) Field of Classification Search
CPC ... A61K 31/195; A61K 31/265; C07C 327/34
USPC .......................................... 514/562; 558/257
See application file for complete search history.

(56) References Cited

FOREIGN PATENT DOCUMENTS

WO    2009100431 A1    8/2009
WO    2013016727 A1    1/2013

OTHER PUBLICATIONS

International Search Report and Written Opinion, dated Jan. 9, 2015 in corresponding application No. PCT/US2014/064581.
Li S, et al., Organocatalysis with cysteine derivatives: recoverable and cheap chiral catalyst for direct aldol reactions, Res Chem Inter, Jun. 15, 2011, 38(1), 195-205.
Wang, K, et al., Redox-sensitive shell cross-linked PEG-polypeptide hybrid micelles for controlled drug release, Poly Chem, Jan. 1, 2012, 3(4) 1084.
Ibrahim M, et al., Macrocyclic peptoids by selective s-acylation of cysteine esters, Synthesis, Feb. 2, 2013, 45 (6), 767-772.
El-Gendy BM, et al., [alpha]-substitution effects on the ease of S—N-acyl transfer in aminothioesters, Chem Bio Drug Design, Apr. 24, 2013, 81(5), 577-582.

*Primary Examiner* — Jennifer M Kim
(74) *Attorney, Agent, or Firm* — Wood, Phillips, Katz, Clark & Mortimer (57) ABSTRACT

A novel substituted N-acetyl-L-cysteine (NAC) derivative and methods of using this compound for the treatment of diseases and/or conditions, including but not limited to diseases and/or conditions of, or involving, the Central Nervous System (CNS), including schizophrenia adrenoleukodystrophy, mitochondrial diseases (e.g. Leigh syndrome, Alpers' disease, and MELAS), Huntington's disease, trichotillomania, HIV-associated neurocognitive disorder, hypoxic-ischemic encephalopathy, drug craving, and drug addiction.

3 Claims, 4 Drawing Sheets

ETHYL (2R)-2-ACETAMIDO-3-(4-METHYLBENZOYL SULFANYL)PROPANOATE AND USES THEREOF

FIELD OF THE INVENTION

This invention relates to a novel substituted N-acetyl-L-cysteine ("NAC") derivative and methods of using this compound for the treatment of diseases and/or conditions, including but not limited to diseases and/or conditions of or involving, the Central Nervous System (CNS), including schizophrenia adrenoleukodystrophy, mitochondrial diseases (e.g. Leigh syndrome, Alpers' disease, and MELAS), Huntington's disease, trichotillomania, HIV-associated neurocognitive disorder, hypoxic-ischemic encephalopathy, drug craving, and drug addiction.

BACKGROUND OF THE INVENTION

Schizophrenia is a debilitating disorder afflicting 1% of the world's population. The development of effective medications to treat schizophrenia relies on advances in characterizing the underlying pathophysiology. Chlorpromazine and other phenothiazines are considered first generation antipsychotics (termed "typical antipsychotics") useful in the treatment of schizophrenia.

Adrenoleukodystrophy, or X-linked adrenoleukodystrophy, is an inherited life-threatening metabolic rare disease. It primarily affects myelination throughout the nervous system, the adrenal cortex, and the Leydig cells in the testes where very-long chain fatty acids accumulate. The adrenoleukodystrophy patient population is heterogeneous, with clinical phenotypes that include progressive neurodegenerative decline leading to vegetative state in children (childhood cerebral X-linked adrenoleukodystrophy). Treatments for adrenoleukodystrophy are include hematopoietic stem cell transplant, which results in a high-survival rate (92% 5-year survival; Peters et al. "Cerebral X-linked adrenoleukodystrophy: the international hematopoietic cell transplantation experience from 1982 to 1999." Blood. 2004; 104:881-888.); however, this treatment is limited to and effective with only a small adrenoleukodystrophy subpopulation, with success typically coming when it is performed in the early stages of the disease.

Adrenoleukodystrophy patients have one or more mutations to the ABCD1 gene, which encodes the peroxisomal ATP-binding cassette transporter. Subsequently, very-long chain fatty acids build up in affected cells, leading to oxidative stress and eventually metabolic failure resulting in cell death, features common to human patients and animal models (Fourcade, S, et al. "Early oxidative damage in neurodegeneration Underlying X-adrenoleukodystrophy." Human Molecular Genetics, 2008; 17: 1762-1773; López-Erauskin, J et al. "Antioxidants halt axonal degeneration in a mouse model of X-adrenoleukodystrophy." Annals of Neurology, 2011; 70:84-92).

Antioxidant therapy is a promising therapy for the treatment of adrenoleukodystrophy and other diseases that involve oxidative stress. At the cellular level, antioxidants have been demonstrated to normalize biomarkers of oxidative stress. N-acetylcysteine ("NAC") is a prodrug of cysteine, which serves as the limiting reagent in the synthesis of glutathione, the body's major antioxidant. When given as an adjuvant therapy to hematopoietic stem cell transplant in advanced stage childhood cerebral X-linked adrenoleukodystrophy patients, patient survival outcome greatly improves with NAC treatment (Miller W et al. "Outcomes after allogeneic hematopoietic cell transplantation for childhood cerebral adrenoleukodystrophy: the largest single-institution cohort report, 2011; 118:1971-1978; Tolar, J et al. "N-acetyl-L-cysteine improves outcome of advanced cerebral adrenoleukodystrophy." Bone Marrow Transplant, 2007; 39:211-215). However, brain penetrance is low and the long-term risks and benefits remain unknown.

Inherited mitochondrial diseases (e.g. Leigh syndrome, Alpers' disease, and MELAS) affecting the CNS are highly variable, and often result in the progressive loss, or dysfunction, of neurons or neuroglial cells. In many cases, the pathogenesis is a result of disruption of mitochondrial respiratory chain processes, which can then increase the generation of reactive oxidative species (ROS), due to mutations in mitochondrial or nuclear DNA. Antioxidant therapy, specifically N-acetylcysteine, acts to decrease ROS and increases glutathione levels, which concomitantly increase cell survival and function.

A range of other diseases share common pathophysiology with abnormal glutamate signaling and heightened levels of oxidative stress, particularly with System $x_c-$, a glutamate-cystine antiporter. Therefore, by engaging a single target, e.g. System $x_c-$, which is at the junction of two distinct metabolic pathways, NAC, NAC derivatives and related molecules, may effectively treat these wide-ranging, and seemingly unrelated, diseases and disorders. This has been partially demonstrated in clinical study with NAC treatment of trichotillomania (Grant, J E, et al. "N-Acetylcysteine, a Glutamate Modulator, in the Treatment of Trichotillomania." Arch Gen Psychiatry, 2009; 66: 756-763). System $x_c-$, NAC, and disturbances in glutamate signaling and oxidative stress are also linked to other diseases that include, but are not limited to, Huntington's disease (Frederick, N M, et al. "Dysregulation of system xc(−) expression induced by mutant huntingtin in a striatal neuronal cell line and in R6/2 mice." Neurochem Int, 2014; 76: 59-69), hypoxic-ischemic encephalopathy (Wang, X, et al. "N-acetylcysteine reduces lipopolysaccharide-sensitized hypoxic-ischemic brain injury." Ann Neurol, 2007; 61: 263-271), HIV-associated neurocognitive disorder (Vázquez-Santiago F J, et al. "Glutamate metabolism and HIV-associated neurocognitive disorders." J Neurovirol, 2014; 20: 315-331).

Schizophrenia may be associated with abnormal glutamate signaling and diminished glutathione levels. Impaired cystine-glutamate antiporter activity can lead to increased oxidative stress and depleted glutathione, as well as abnormal glutamate neurotransmission, synaptic connection, and gene expression, all of which are observed in schizophrenia. In addition, impaired cystine-glutamate antiporter activity and faulty glutamate neurotransmission bear on the issue of uncontrolled drug use, i.e., drug addiction.

Cysteine prodrugs, such as NAC, drive cystine-glutamate exchange by apparently elevating extracellular cystine levels, thereby creating a steep cystine concentration gradient.

However, alternatives to NAC are needed. NAC undergoes extensive first pass metabolism requiring the usage of high doses that limit the utility of the drug and, potentially, increase the chances of side effects due to the buildup of metabolized by-products. The compound of the present invention is designed to substantially avoid the problem of first pass metabolism and therefore exhibit increased efficacy as compared to NAC and other prior cysteine prodrugs. In addition, NAC demonstrates poor CNS penetration due to an inability to cross the blood brain barrier.

Accordingly, there is a need for novel compounds that would have a reduced incidence of problems associated with NAC. The compound of the present invention is designed to substantially avoid the problems of first pass metabolism and poor CNS bioavailability, thereby exhibiting increased efficacy as compared to NAC and other prior cysteine prodrugs.

SUMMARY OF THE INVENTION

In one aspect, the present invention is directed to a compound of formula I:

I

This compound can be referred to as ethyl (2R)-2-acetamido-3-(4-methylbenzoylsulfanyl)propanoate and is referred to throughout the specification as Pro-4051.

The invention also encompasses pharmaceutically acceptable salts, esters or prodrugs of this compound.

In another aspect, the invention is directed to a method of treating a disease or condition in a subject comprising administering to the subject a therapeutically effective amount of a compound of Formula I or a pharmaceutically acceptable salt ester or prodrug thereof. The preferred route of administering to the subject is via oral delivery. Preferably, diseases or conditions treatable with the compound of the present invention are related to the CNS.

In a preferred embodiment, the disease is schizophrenia.

In another aspect, the invention provides a method of treating drug craving in a subject comprising administering to the subject a therapeutically effective amount of a compound of Formula I or a pharmaceutically acceptable salt ester or prodrug thereof. The preferred route of administering to the subject is via oral delivery.

The invention further encompasses pharmaceutical compositions containing a compound of Formula I or a pharmaceutically acceptable salt, ester or prodrug thereof in combination with a pharmaceutically-acceptable carrier.

Methods of formulating/manufacturing such pharmaceutical compositions (alternatively termed "medicaments") for the treatment of a disease or condition in a subject are also within the invention's scope.

DETAILED DESCRIPTION OF THE INVENTION

The following definitions are used, unless otherwise described.

The term "prodrug" refers to compounds, including monomers and dimers of the compound of the invention, which have cleavable groups and become under physiological conditions compounds which are pharmaceutically active in vivo.

The term "ester" refers to compounds having a generic structure of $RCO_2R'$, where R and R' are the organic parts of the carboxylic acid and alcohol respectively.

The term "subject" includes mammals. Mammals include but are not limited to humans. The terms "patient" and "subject" are used interchangeably.

The term "therapeutically effective amount" means the amount of a compound that, when administered to a subject for treating a disease or disorder, is sufficient to effect such treatment for the disease or disorder. The "therapeutically effective amount" can vary depending on the compound, the disease or disorder and its severity, and the age, weight, etc., of the subject to be treated.

The terms "treating" or "treatment" of any disease or disorder refer, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder, or even preventing the same.

In one aspect, the present invention is directed to a compound of formula I:

I

The invention also encompasses pharmaceutically acceptable salts, esters or prodrugs of this compound.

The compound of the invention may exist in different isomeric (e.g. enantiomers and distereoisomers) forms. The invention contemplates all such isomers both in pure form and in admixture, including racemic mixtures. Enol forms are also included.

The compound of the invention can exist in unsolvated as well as solvated forms, including hydrated forms, e.g., hemihydrate. In general, the solvated forms, with pharmaceutically acceptable solvents such as water, ethanol, and the like are equivalent to the unsolvated forms for the purposes of the invention.

The compound of the invention also forms pharmaceutically acceptable salts, e.g., acid addition salts. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in J. *Pharmaceutical Sciences,* 1977, 66: 1 et seq. For example, for acid addition salts the nitrogen atoms may form salts with acids. Examples of suitable acids for salt formation are hydrochloric, sulfuric, phosphoric, acetic, citric, oxalic, malonic, salicylic, malic, furmaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.,* 66: 1-19 (1977) which is incorporated herein by reference.)

As used herein, the term "composition" is intended to encompass a product comprising the specified ingredients in the specified amounts, as well as any product which results, directly or indirectly, from a combination of the specified ingredients in the specified amounts.

The compound of the present invention can be used in the form of pharmaceutically acceptable salts derived from inorganic or organic acids. The salts can be prepared in situ during the final isolation and purification of the compound of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of the compound of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Dosage forms for topical administration of the compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of the compound of the present invention can be employed in pure form or, where such forms exist, in pharmaceutically acceptable salt, ester or prodrug form. Alternatively, the compound can be administered as a pharmaceutical composition containing the compound of interest in combination with one or more pharmaceutically acceptable excipients.

The phrase "therapeutically effective amount" of the compound of the invention means a sufficient amount of the compound to treat disorders, at a reasonable benefit/risk ratio applicable to any medical treatment. It will be understood, however, that the total daily usage of the compound and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compound of this invention administered to a human or lower animal may range from about 0.0001 to about 2000 mg/kg/day. For purposes of oral administration, more preferable doses can be in the range of from about 0.001 to about 15 mg/kg/day, with the most preferable dose being in the range of from about 0.001 to about 5 mg/kg/day. If desired, the effective daily dose can be divided into multiple doses for purposes of administration; consequently, single dose compositions may contain such amounts or submultiples thereof to make up the daily dose.

The present invention also provides pharmaceutical compositions that comprise the compound of the present invention formulated together with one or more pharmaceutically acceptable carriers. The pharmaceutical compositions can be specially formulated for oral administration in solid or liquid form, for parenteral administration or for rectal administration.

The pharmaceutical compositions of this invention can be administered to humans and other mammals orally, rectally, parenterally, intracisternally, intravaginally, transdermally (e.g. using a patch), transmucosally, sublingually, pulmonary, intraperitoneally, topically (as by powders, ointments or drops), bucally or as an oral or nasal spray. The terms "parental" or "parenterally," as used herein, refers to modes of administration which include intravenous, intramuscular, intraperitoneal, intrasternal, subcutaneous and intraarticular injection and infusion.

In another aspect, the present invention provides a pharmaceutical composition comprising a component of the present invention and a physiologically tolerable diluent. The present invention includes the compound as described above formulated into compositions together with one or more physiologically tolerable or acceptable diluents, carriers, adjuvants or vehicles that are collectively referred to herein as diluents, for parenteral injection, for intranasal delivery, for oral administration in solid or liquid form, for rectal or topical administration, among others.

Compositions suitable for parenteral injection may comprise physiologically acceptable, sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), vegetable oils (such as olive oil), injectable organic esters such as ethyl oleate, and suitable mixtures thereof.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol, glycerol monostearate, and PEG caprylic/capric glycerides; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols, and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Compositions for rectal or vaginal administration are preferably suppositories which can be prepared by mixing the compound of this invention with suitable non-irritating excipients or carriers such as cocoa butter, polyethylene glycol or a suppository wax which are solid at room temperature but liquid at body temperature and therefore melt in the rectum or vaginal cavity and release the active compound.

The compound of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., *Methods in Cell Biology*, Volume XIV, Academic Press, New York, N.Y. (1976), p. 33 et seq.

In another aspect, the invention is directed to a method of treating a disease or condition in a subject comprising administering to the subject a therapeutically effective amount of the compound of Formula I or a pharmaceutically acceptable salt ester or prodrug thereof. The preferred route of administering to the subject is via oral delivery.

Preferably, diseases or conditions treatable with the compound of the present invention are related to the CNS. In a preferred embodiment, the disease is schizophrenia.

However, it is within a skill in the art that the provided compound may be used to treat other diseases or conditions associated with diminished glutathione levels and/or glutamate signaling, and/or oxidative stress, and/or impaired cystine-glutamate antiporter activity, glutamate neurotransmission, synaptic connection, and gene expression.

In general, the invention is not limited to treatment of any specific disease or condition but encompasses the treatment of any disease or condition whose mechanism may be affected by the compound of the present invention.

In another aspect, the invention provides a method of treating drug craving in a subject comprising administering to the subject a therapeutically effective amount of the compound of Formula I or a pharmaceutically acceptable salt, ester or thereof. The preferred route of administering to the subject is via oral delivery.

The invention further encompasses pharmaceutical compositions containing the compound of Formulas I or a pharmaceutically acceptable salt, ester or prodrug thereof in combination with a pharmaceutically-acceptable carrier.

Methods of formulating/manufacturing such pharmaceutical compositions (alternatively termed "medicaments") for the treatment of a disease or condition in a subject are also within the invention's scope.

For a clearer understanding of the invention, Examples are provided below. These are merely illustrations and are not to be understood as limiting the scope of the invention in any way. Indeed, various modifications of the invention in addition to those shown and described herein will become apparent to those skilled in the art from the following examples and foregoing description. Such modifications are also intended to fall within the scope of the appended claims.

EXAMPLES

Example 1

Synthesis Strategies

General Methods

$^1$H-NMR spectra were obtained on a Varian Mercury 300-MHz NMR. Purity (%) was determined with a Waters Alliance 2695 HPLC (Waters Symmetry C18, 4.6×75 mm, 3.5 μm) with a 2996 diode array detector from 210-400 nm.

Synthesis of Ethyl (2R)-2-acetamido-3-(4-methyl-benzoylsulfanyl)propanoate (Pro-4051)

2-Acetylamino-3-(4-methyl-benzoylsulfanyl)-propionic acid

To a solution of benzotriazole (9.91 g, 83.2 mmol) in tetrahydrofuran (80 mL) was added 4-methylbenzoyl chloride (5.0 mL, 37.8 mmol) (5 g, 95%). After 2 hours, the resulting slurry was filtered and the solid was rinsed with tetrahydrofuran (25 mL). The filtrates were combined and added to a solution of N-acetyl-L-cysteine (5.55 g, 34.0 mmol) and N-methylmorpholine (3.74 mL, 34.0 mmol) in tetrahydrofuran (50 mL) at 0° C. The resulting mixture was allowed to warm to ambient temperature over 16 hours. Aqueous hydrochloric acid (1 M, 100 mL) was added to the mixture and the resulting mixture was concentrated at reduced pressure to a volume of approximately 125 mL. Additional aqueous hydrochloric acid (80 mL) was added and the mixture was extracted with dichloromethane (180 mL then 80 mL). The combined organic extracts were combined, dried over sodium sulfate, filtered and concentrated at reduced pressure. Ethyl acetate (100 mL) was added and the resulting slurry was stirred for 2 hours. The resulting slurry was filtered and dried to give a white solid (5.7 g, 60%). $^1$H NMR (300 MHz, DMSO) δ=12.94 (s, 1H), 8.34 (d, J=7.9 Hz, 1H), 7.86-7.74 (m, 2H), 7.35 (d, J=8.5 Hz, 2H), 4.43 (dt, J=5.0, 8.4 Hz, 1H), 3.53 (dd, J=5.0, 13.8 Hz, 1H), 3.21 (dd, J=8.5, 13.8 Hz, 1H), 2.37 (s, 3H), 1.83 (s, 3H). MS (ESI) m/z 282 (M+1)$^+$.

Ethyl (2R)-2-acetamido-3-(4-methylbenzoylsulfanyl) propanoate

To a solution of 2-acetylamino-3-(4-methyl-benzoylsulfanyl)-propionic acid (1.1 g, 3.91 mmol) and triethylamine (0.68 mL, 4.89 mmol) N,N-dimethylformamide (5 mL) was added iodoethane (0.39 mL, 4.89 mmol) and the resulting solution was stirred at ambient temperature for 18 hours. The reaction mixture was added slowly to water (50 mL) with rapid stirring. After stirring for 2 hours, the resulting slurry was filtered and the solid was rinsed with water and dried under vacuum to give the product as a white solid (780 mg, 60%). $^1$H NMR (300 MHz, DMSO) δ=8.47 (d, J=7.9 Hz, 1H), 7.81 (s, 1H), 7.80-7.78 (m, 1H), 7.35 (d, J=7.6 Hz, 2H), 4.46 (dt, J=5.3, 8.1 Hz, 1H), 4.09 (q, J=6.8 Hz, 2H), 3.50 (dd, J=5.4, 13.6 Hz, 1H), 3.24 (dd, J=8.2, 13.8 Hz, 1H), 2.37 (s, 3H), 1.83 (s, 3H), 1.16 (t, J=7.0 Hz, 3H). MS (ESI) m/z 310 (M+1)$^+$.

Example 2

In Vitro Studies $^{14}$C Uptake by Pro-4051

The goal of these experiments was to determine $^{14}$C-cystine uptake. The experiments were conducted as follows.

The screening of the compound was performed using an in vitro culture system of human glial cells from brain astrocytoma (1321N1). Cells were plated on 24 well plates coated with poly-D-lysine and laminin and grown in a balanced salt solution supplemented with 5% heat inactivated horse serum, 5% fetal bovine serum, 2 mM glutamine and glucose (total 21 mM). Cultures were maintained in humidified 5% $CO_2$ incubators at 37° C. for 3-4 days before experiments were performed, at this time the cultures has formed a single confluent layer. For experiments, cultures were washed 3 times into a Na-free HEPES and $HCO_3^-$ buffered balanced salt solution. After 1 hour the test compounds are added. Following a three hour incubation, $^{14}$C-cystine (0.025 mCi/mL) was then added for 20 minutes. Following the $^{14}$C-cystine exposure, cultures were washed 3 times with ice cold HEPES buffered saline solution and dissolved in 250 μl sodium dodecyl sulfate (0.1%). An aliquot (200 μl) was removed and added to scintillation fluid for counting. Values were normalized to $^{14}$C-cystine uptake in untreated controls on the same experimental plate.

$^3$H-Glutamate Release by Pro-4051

This assay also uses the cell culture system of human glial cells from brain astrocytoma (1321N1) described above. Initially, cells are washed with HBBSS, and $^3$H-glutamate is added (PerkinElmer: 1 mCi/mL stock solution is diluted (30 μL+500 μL HBBSS) and 10 μL of diluted radiolabel is added to each well). Following a 1 hour incubation to load the cells with the labeled glutamate, the cells are washed again with HBBSS, and the drug is added. At 30, 90, and 180 minutes, 50 μL of extracellular media is sampled from each well and is measured using a Beckman LS 6500 scintillation counter.

Figure 1:
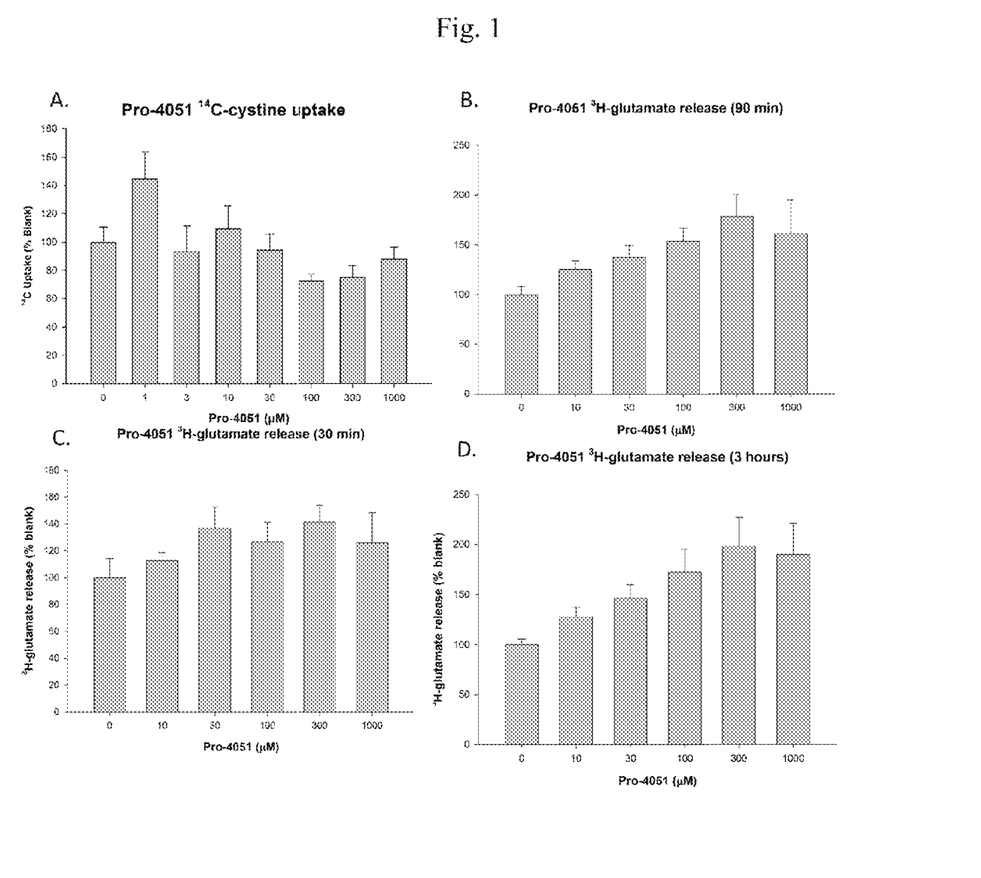
FIG. 1 is a graphical representation of the $^{14}C$-cystine uptake and $^{3}H$-glutamate release by Pro-4051 as a percentage of the control.

Results of the $^{14}$C-cystine uptake and $^3$H-glutamate release by astrocytes treated with differing concentrations of Pro-4051, are presented in FIG. 1, as a percentage of the untreated control. The most effective concentration of Pro-4051 was 100 μM which produced an approximately 28% decrease in $^{14}$C-cystine uptake demonstrating inhibition of $^{14}$C-cystine uptake by a process not limited to an alternate substrate, a cystine-glutamate antiporter inhibitor, and an effective prodrug. This graph represents an average of three experiments run. Pro-4051 is not in solution above 316 μM according to solubility data. The most effective concentration of Pro-4051 for $^3$H-glutamate release was 300 μM which produced an approximately 100% increase at 3 hours and is evidence that the $^{14}$C-cystine uptake is being inhibited by direct competition from Pro-4051.

In Vitro Thiol Experiments

To further resolve by what process the inhibition of $^{14}$C-cystine uptake is occurring intracellular cysteine levels were determined.

The experiment was conducted as follows.

Mixed cortical cell cultures containing glial and neuronal cells were prepared from fetal (15-16 day gestation) mice as previously described (Lobner D, Comparison of the LDH and MTT assays for quantifying cell death: validity for neuronal apoptosis?, *J Neurosci Methods*, 2000, Mar. 15, 96(2), 147-152). Dissociated cortical cells were plated on 24-well plates coated with poly-D-lysine and laminin in Eagles' Minimal Essential Medium (MEM, Earle's salts, supplied glutamine-free) supplemented with 5% heat-inactivated horse serum, 5% fetal bovine serum, 2 mM glutamine and glucose (total 21 mM). Cultures were maintained in humidified 5% $CO_2$ incubators at 37° C. Mice were handled in accordance with a protocol approved by our institutional animal care committee and in compliance with the Public Health service Policy on Humane Care and Use of Laboratory Animals.

Mixed cortical cell cultures, 14 days in vitro (this allows for a confluent layer of astrocytes to form and the neurons to generate a complex network of axons and dendrites), were washed into bicarbonate buffered salt solution. After 1 hour, 3, 10, 30, 100 μM of Pro-4051 was added and the cells were incubated for 30 or 90 minutes, after which the cells were thoroughly washed and the collected in 250 μL of aqueous mobile phase (50 mM citric acid, 10 mM octanesulfonic acid, pH 2.8) was added, after 10 minutes at 37° C. the cells were scraped from the plates and transferred to 1.5 mL tubes for analysis.

Samples were then sonicated with a Fisher Scientific 60 Sonic Dismembrator. One fraction of this homogenate was analyzed with the Pierce BCA (bicinchoninic acid) method to determine protein concentration. The other fraction was filtered using 3 K molecular weight cutoff, polyethersulfone centrifugal protein filters, and analyzed for thiol content using HPLC (ALF-115 column, 150×1.0 mm, 3 μm C18; mobile phase: 50 mM citric acid, 10 mM octanesulfonic acid, 2% acetonitrile, pH 2.8, 50 uL/min flow rate) with electrochemical detection (Decade II, Au working electrode, Flex Cell HyREF, 0.55V, Antec Leyden, Netherlands).

Figure 2:
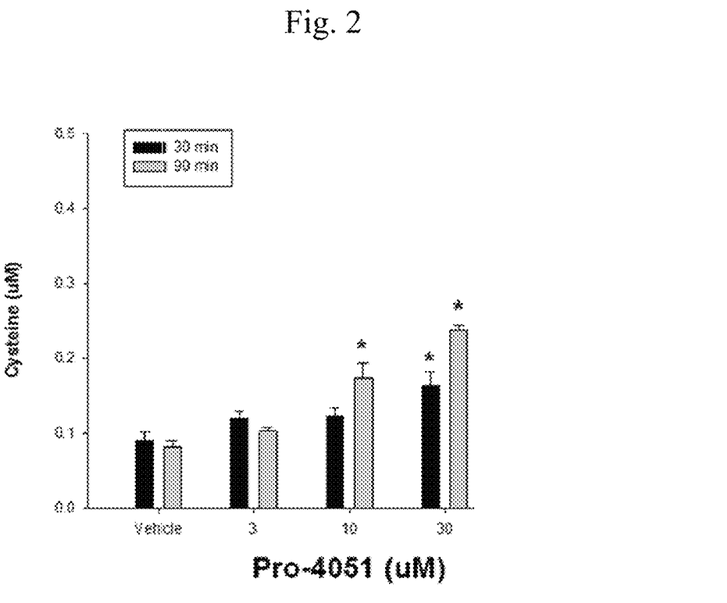
FIG. 2 is a graphical representation of the amount of intracellular cysteine.

When the intracellular thiol assay was initiated, all data was normalized to protein concentration. However, the protein method did not produce consistent results in control samples, so that method of normalization was abandoned. The data presented herein represents the raw cysteine concentrations in the collected samples. FIG. 2 demonstrates that administration of Pro-4051 at 100 μM increases intracellular cysteine concentration to 0.36 μM at 90 minutes (approximately 4 times that of the control). This result demonstrates that Pro-4051 was effectively cleaved, yielding an increase in intracellular cysteine. Thus, based on the 3 in vitro experiments it is apparent that Pro-4051 behaves as an effective cysteine prodrug.

Example 4

In Vivo Studies

Prepulse Inhibition Experiment

The goal of this experiment was to demonstrate the efficacy of the test compounds in a predictive animal model of schizophrenia.

The experiment was conducted as follows.

Rats were placed on a platform in a sound attenuating chamber (10.875"×14"×19.5"; Hamilton Kinder, CA) that rested on a motion sensing plate. During all sessions, the background noise was held constant at 60 dB. A matching session was conducted to determine the magnitude of the average startle response for each rat. This session consisted of a five minute habituation period followed by 20 trials; 17 trials involved the presentation of a single auditory stimulus (pulse stimulus; 50 dB above the background noise) and three trials in which a pre-pulse stimulus (12 db above background) was presented 100 ms before the pulse auditory stimulus. Rats were then assigned into the various treatment groups so that the magnitude of the startle response was equivalent across all groups. Two days later, a testing session was conducted to assess sensorimotor gating. One hour prior to testing, rats received a prodrug (0-100 mg/kg, P.O.) and 55 minutes later acute MK-801 maleate (0.1 mg/kg, SC). The testing session consisted of a five minute habituation period, after which rats received 58 discrete trials; 26 trials during which the pulse stimulus (50 db above background) was presented alone, eight trials each in which the pulse stimulus was preceded by a prepulse stimulus (5, 10, or 15 db above background) and eight background trials with no pulse (No stimulus; background noise only). The first six pulse alone trials were not included in the average startle stimulus to achieve a relatively stable level of startle reactivity. All startle responses were normalized to vehicle control, and the percent of prepulse inhibition was determined as 100−(average prepulse startle response/average startle stimulus alone)*100.

Figure 3:
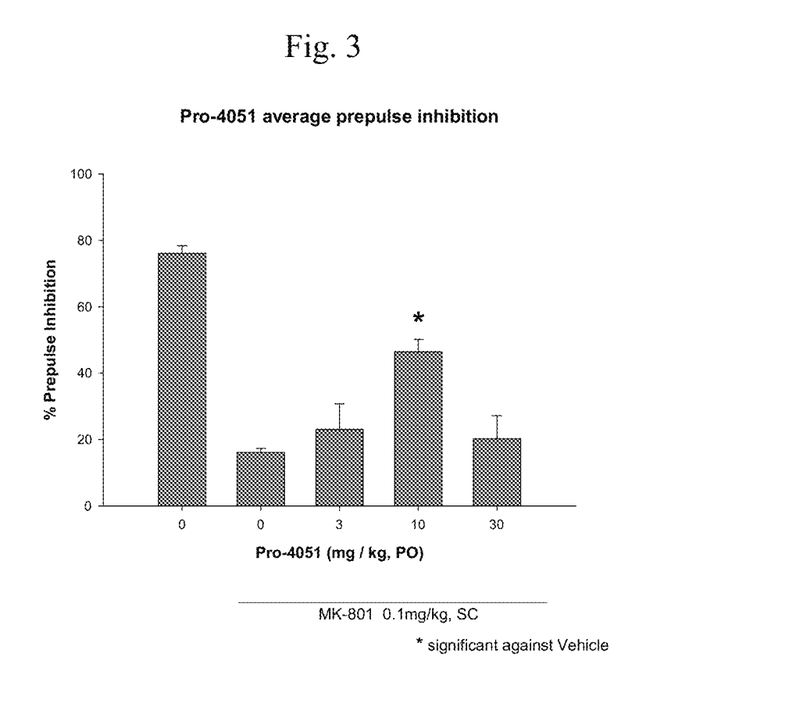
FIG. 3 is a graphical representation of prepulse inhibition for Pro-4051.

FIG. 3 demonstrates the results of the experiment for Pro-4051.

As the bar graph in FIG. 3 demonstrates, at 10 mg/kg concentration, % prepulse inhibition was about 46%, as compared to about 16% for the control group that received both MK-801 and vehicle.

These results indicate that this compound significantly ameliorates the schizophrenia-like MK-801-induced deficit in prepulse inhibition.

Elevated-Plus Maze

The goal of this experiment was to demonstrate the ability of the test compounds to penetrate the CNS in an animal model of anxiety.

The experiment was conducted as follows.

Rats were tested in a standard elevated plus maze; testing occurred in a dimly illuminated room using only two lights mounted over the maze. Animals were allowed to habituate to the room for at least one hour prior to treatment. One hour prior to testing, rats received a compound of the present invention (0-10 mg/kg, P.O.). For testing, the rat was placed in the elevated plus maze for five minutes, alternating the starting position between facing an open arm and facing a closed arm. The session was recorded and an observer blind to treatment recorded the number of explorations, entries and time spent in the open arm. Explorations were defined as the rat placing two feet into an open arm without fully entering said arm. Entries were defined as the rat placing all four feet in an open arm. Time of entry in the open arm was recorded from the time the rat placed four feet in the open arm until two of the rats' feet entered the open square.

Figure 4:
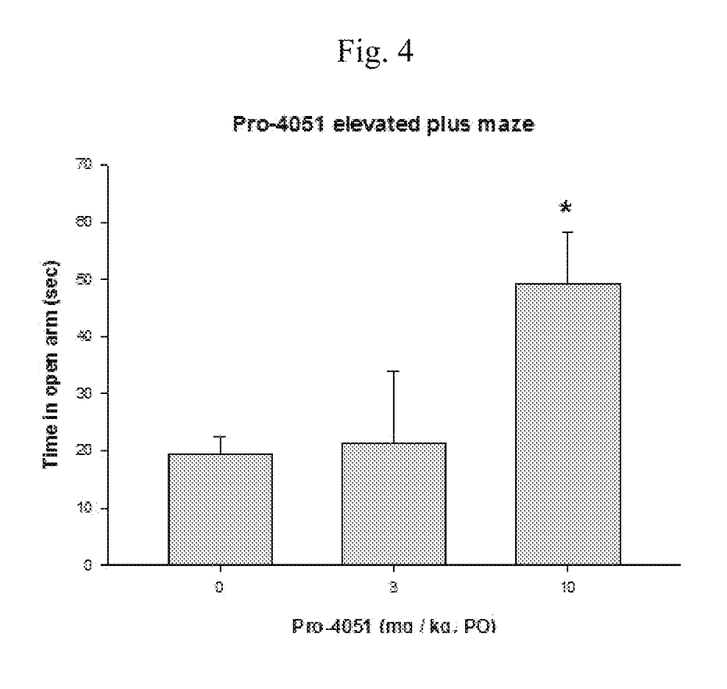
FIG. 4 is a graphical representation of the total time spent in the open arms of the elevated plus maze.

After administration of a compound of the present invention, the rat increased the amount of time spent on the open arms of the maze, demonstrating a reduced anxiety and effective alleviation of symptoms associated with schizophrenia. Specifically, as seen in FIG. 4, rats treated with 10 mg/kg, PO (orally) of Pro-4051 spent around 48 seconds on the open arms. This represents an increase of time spent on the open arm over control of about 150%. Thus, Pro-4051 demonstrates the ability to alleviate symptoms associated with schizophrenia in vivo.

Brain Levels of NAC Following Oral Administration of Pro-4051

The goal of this experiment was to demonstrate the pharmacokinetic properties of Pro-4051 in the brain of C57BL/6 mice.

The experiment was conducted as follows.

Pro-4051 was administered orally to C57BL/6 mice at 100 mg/kg. Brain samples were collected at 0.25, 0.50, 1, 2 and 4 hours following the oral administration. Levels of NAC were quantified in the brain samples using liquid chromatography-mass spectrometry (LC-MS/MS).

Figure 5:
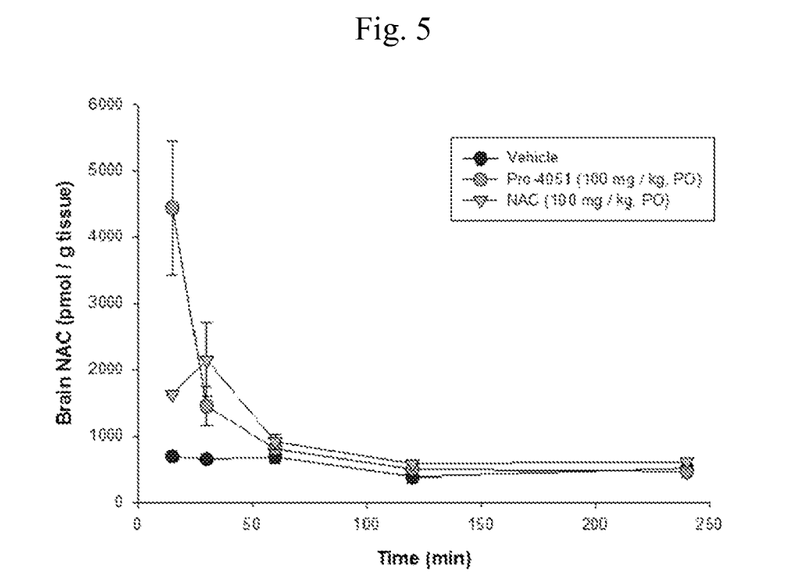
FIG. 5 is a graphical representation of levels of NAC present in the brain after oral administration of Pro-4051.

FIG. 5 depicts the levels of NAC found in the brain following oral administration of Pro-4051. At 0.25 hours oral administration of Pro-4051 caused NAC to occur in the brain at about 4,500 pmol/g of brain tissue or about 6 times that of the vehicle (about 750 pmol/g). Surprisingly, at the same time point, oral administration of Pro-4051 caused NAC to occur in the brain about 3 times than the oral administration of NAC itself (about 1,500 pmol/g).

Figure 6:
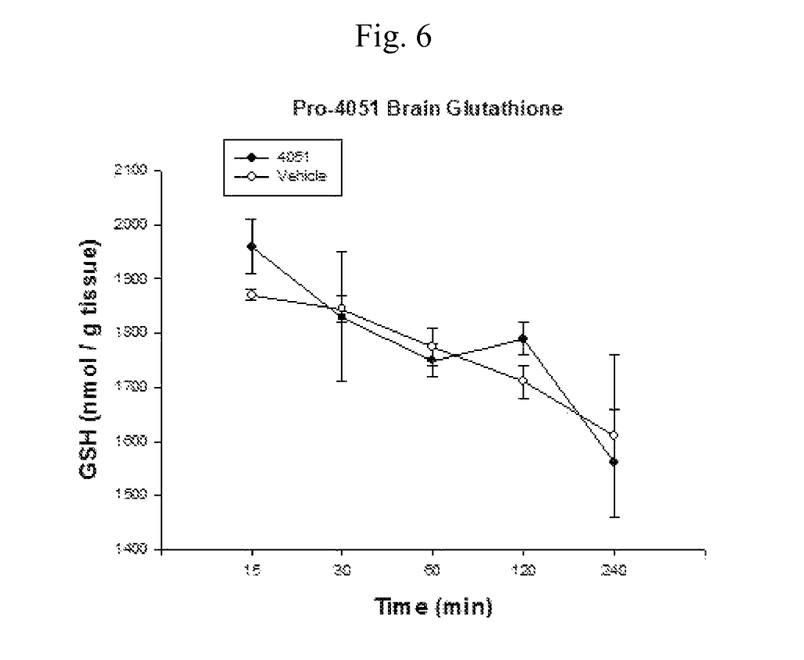
FIG. 6 is a graphical representation of levels of glutathione present in the brain after oral administration of Pro-4051.

FIG. 6 depicts the levels of glutathione found in the brain following oral administration of Pro-4051. At 4.0 hours oral administration of 100 mg/kg of Pro-4051 caused glutathione to occur in the brain at about 1960 nmol/g of brain tissue or about 1.05 times that of the vehicle (about 1870 nmol/g).

These results demonstrate that oral administration of Pro-4051 is able to more effectively elevate levels of NAC in the brain than the oral administration of NAC itself and thus may be more effective than NAC for the treatment of CNS diseases, such as schizophrenia, that currently respond to large doses of NAC.

What is claimed is:

1. A compound of formula I, or a pharmaceutically acceptable salt or ester thereof.

2. A pharmaceutical composition comprising the compound of claim 1 and a pharmaceutically acceptable carrier.

3. A method of treating schizophrenia comprising administering to a subject in need thereof a therapeutically effective amount of the compound of claim 1.

* * * * *